United States Patent [19]

Miller

[11] Patent Number: 4,942,354
[45] Date of Patent: Jul. 17, 1990

[54] PROCESS FOR MONITORING THE EFFECTIVENESS OF REPAIRS MADE TO ZONES OF REINFORCED CONCRETE STRUCTURES

[76] Inventor: John B. Miller, Bergtunvn. 9B, N-1084 Oslo 10, Norway

[21] Appl. No.: 368,994

[22] Filed: Jun. 16, 1989

Related U.S. Application Data

[63] Continuation-in-part of Ser. No. 83,718, Aug. 10, 1987, abandoned.

[30] Foreign Application Priority Data

Aug. 29, 1986 [CH] Switzerland ............... 3472/86

[51] Int. Cl.⁵ .............................. G01N 27/26
[52] U.S. Cl. ............................. 324/71.2; 204/404; 204/153.1
[58] Field of Search ............... 204/404.1 R; 324/71.1, 324/71.2, 65 CR, 65 R, 693, 700

[56] References Cited

U.S. PATENT DOCUMENTS

| | | | |
|---|---|---|---|
| 3,999,121 | 12/1976 | Taylor, Jr. | 324/65 CR |
| 4,003,815 | 1/1977 | Ikeda et al. | 324/71.2 |
| 4,209,376 | 6/1980 | Arita et al. | 204/195 |
| 4,347,429 | 8/1982 | Will | 338/80 |
| 4,481,474 | 11/1984 | Gerrit | 324/65 CR X |
| 4,623,434 | 11/1986 | Nicholson et al. | 204/1 C |

FOREIGN PATENT DOCUMENTS

| | | |
|---|---|---|
| 0216628 | 4/1987 | European Pat. Off. . |
| 2755644 | 6/1978 | Fed. Rep. of Germany . |
| 1550326 | 12/1968 | France . |
| 1584506 | 2/1981 | United Kingdom . |
| 2157441 | 10/1985 | United Kingdom . |

OTHER PUBLICATIONS

Patent Abstracts of Japan, 19 Apr. 1985, vol. 9, No. 90, P-350, JPA 59 217 147, 59-217147.
McKenzie, "Techniques for Monitoring Corrosion of Steel in Concrete," Corrosion Prevention & Control, Feb. 1987, pp. 11-17.
Andrade et al., "Quantitative Measurements of Corrosion . . . ," Werkstoffe und Korrosion, 29, 515-519 (1978).

Primary Examiner—Reinhard J. Eisenzopf
Assistant Examiner—Jack B. Harvey
Attorney, Agent, or Firm—Richard Bushnell

[57] ABSTRACT

A process is described which makes it possible to locate, on the surface, those zones of reinforced concrete structures which have been damaged or are liable to be damaged by corrosion of the metal strengthening elements embedded in the concrete, with a view to repairing the zones. A process is also described which makes it possible to monitor, continuously or intermittently, the effectiveness of the repairs made to reinforced concrete structures.

1 Claim, 3 Drawing Sheets

FIG. 3

| | 0 | 0,5 | 1,0 | 1,5 | 2,0 | 2,5 | 3,0 | 3,5 | m |
|---|---|---|---|---|---|---|---|---|---|
| | 157 | 158 | 144 | 129 | 203 | 307 | 325 | 325 | 0,5 |
| | 153 | 148 | 165 | 177 | 210 | 239 | 377 | 323 | 1,0 |
| 16 | 141 | 152 | 137 | 156 | 193 | 283 | 358 | | 1,5 |
| | 196 | 191 | 173 | 173 | 196 | 256 | 259 | 6a | 2,0 |
| | 214 | 210 | 209 | 191 | 212 | 213 | 244 | | 2,5 |
| | 240 | 256 | 239 | 225 | 242 | 166 | 270 | | 3,0 |
| | 282 | 277 | 255 | 256 | 251 | 280 | 305 | 314 | 3,5 |
| | 318 | 297 | 283 | 287 | 285 | 350 | 335 | 350 | 4,0 |
| | 325 | 293 | 290 | 286 | 290 | 320 | 358 | | 4,5 |
| | 350 | 323 | 296 | 242 | 178 | 229 | 337 | | 5,0 |
| 6a | 246 | 337 | 292 | 257 | 231 | 160 | 268 | 315 | 5,5 |
| | 343 | 362 | 295 | 246 | 187 | 216 | 300 | 313 | 6,0 |
| | 340 | 309 | 274 | 210 | 288 | 321 | 317 | 356 | 6,5 — 16 |
| | 330 | 321 | 150 | 254 | 296 | 247 | 350 | 356 | 7,0 |
| | 310 | 213 | 300 | 258 | 274 | 328 | 351 | 404 | 7,5 |
| | 358 | 361 | 328 | 318 | 225 | 291 | 308 | 326 | 8,0 — 7a |
| | 304 | 323 | 312 | 315 | 338 | 344 | 333 | 345 | 8,5 |
| | 306 | 331 | 317 | 335 | 342 | 333 | 308 | 356 | 9,0 |
| | 317 | 325 | 330 | 331 | 328 | 330 | 258 | 285 | 9,5 |
| | 298 | 282 | 266 | 239 | 281 | 226 | 208 | | 10,0 — 16 |
| | 225 | 310 | 281 | 295 | 280 | 256 | 279 | 290 | 10,5 |
| | 159 | 197 | 228 | 247 | 211 | 242 | 211 | 273 | 11,0 |
| | 112 | 144 | 146 | 142 | 42 | 186 | 205 | 230 | 11,5 |
| | 175 | 82 | 131 | 80 | 112 | 174 | 19 | 33 | 12,0 |
| | 177 | 170 | 205 | 173 | 161 | 155 | 141 | 63 | 12,5 |
| | 200 | 195 | 44 | 202 | 150 | 130 | 110 | 196 | 13,0 |
| | 246 | 160 | 120 | 225 | 247 | 129 | 164 | 154 | 13,5 |
| | 250 | 218 | 124 | 100 | 128 | 29 | 98 | 119 | 14,0 |
| | 212 | 106 | 130 | 128 | 121 | 136 | 144 | 162 | 14,5 |
| | 201 | 180 | 135 | 132 | 138 | 156 | 142 | 231 | 15,0 |
| 6b | 75 | 214 | 135 | 176 | 164 | 147 | 164 | 166 | 15,5 |
| | 200 | 228 | 101 | 128 | 113 | 96 | 111 | 143 | 16,0 |
| | 161 | 287 | 200 | 129 | 126 | 171 | 172 | 147 | 16,5 |
| | 176 | 209 | 85 | 138 | 133 | 99 | 217 | 150 | 17,0 |
| 16 | 176 | 234 | 204 | 199 | 270 | 181 | 244 | 195 | 17,5 |
| | 209 | 206 | 198 | 153 | 129 | 106 | 130 | 100 | 18,0 |
| | 274 | 266 | 256 | 187 | 139 | 128 | 75 | 105 | 18,5 |
| | 140 | 143 | 159 | 80 | 11 | +20 | 95 | 115 | 19,0 |
| | 230 | 228 | 96 | 92 | 171 | 66 | 114 | 117 | 19,5 |
| | 175 | 106 | 165 | 173 | 147 | 80 | 26 | 30 | 20,0 |
| | 200 | 196 | 88 | 122 | 159 | 100 | 130 | 96 | 20,5 |
| | 204 | 157 | 78 | 168 | 103 | 96 | 103 | 109 | 21,0 |
| | 233 | 255 | 105 | 203 | 162 | 85 | 77 | 32 | 21,5 |
| 6c | 166 | 135 | 180 | 224 | 198 | 106 | 39 | 12 | 22,0 |
| | 139 | 216 | 104 | 178 | 150 | 103 | 66 | 99 | 22,5 |
| | 185 | 229 | 180 | 150 | 163 | 55 | 82 | 142 | 23,0 |
| | 152 | 167 | 185 | 200 | 96 | 149 | 103 | 189 | 23,5 |
| | 111 | 164 | 155 | 110 | 50 | 143 | 103 | 50 | 24,0 |

PROCESS FOR MONITORING THE EFFECTIVENESS OF REPAIRS MADE TO ZONES OF REINFORCED CONCRETE STRUCTURES

This application is a continuation of application Ser. No. 083,718, filed Aug. 10, 1987, now abandoned.

SUMMARY OF THE INVENTION

The invention relates to a process which makes it possible to locate, on the surface, those zones of reinforced concrete structures which have been damaged or are liable to be damaged by corrosion of the metal strengthening elements embedded in the concrete, with a view to repairing the said zones.

The invention also relates to a process which makes it possible to monitor, continuously or intermittently, the effectiveness of the repairs made to reinforced concrete structures damaged by corrosion of the metal strengthening elements.

BACKGROUND OF THE INVENTION

Corrosion of the metal strengthening elements used in the building of reinforced concrete structures causes progressive deterioration of the concrete to varying degrees. In its final stage, this deterioration appears in the form of cracks at the surface of the concrete or even splitting of the concrete mass. The difficulty lies in the fact that, in many cases, it is inadvisable to wait until this stage before acting, but, in the absence of any visible phenomenon, identification of the damaged zones of concrete becomes a matter of chance. At the present time, in fact, there are no non-destructive techniques which make it possible to locate the zones damaged by corrosion of the metal strengthening elements, even less the zones which are liable to be damaged in this way at points where corrosion of the said metal elements is still slight.

It is known that ferrous metals, for example steel, tend to corrode. This phenomenon involves an electrochemical process which depends particularly on the oxygen concentration, moisture content and acidity of the ambient medium, and which can be characterized by its electrical potential. In fact, it is known how to measure the corrosion potential of steel bars embedded in concrete by using a reference electrode such as a calomel electrode or an electrode of the Ag/AgCl or Cu/CuSO$_4$ type.

THE INVENTION

It has been found, surprisingly, that these measurements of the corrosion potential of steel can advantageously be utilized to locate, at a distance and without first destroying the mass, those zones of reinforced concrete structures which have been damaged or are liable to be damaged by corrosion of the metal elements, and hence the zones which are in need of repair or preventive treatment. This is achieved by carrying out the process of claim 1.

It has also been found that these measurements of corrosion potential can be used to monitor, continuously or intermittently, the effectiveness of the repairs made to reinforced concrete structures, more precisely by carrying out the process of claim 8.

BRIEF DESCRIPTION OF THE DRAWINGS

The attached drawings illustrate some particular embodiments of the invention without implying a limitation.

FIG. 3 shows a matrix of electrical potentials measured according to the invention.

PREFERRED EMBODIMENTS OF THE INVENTION

Figure 1:
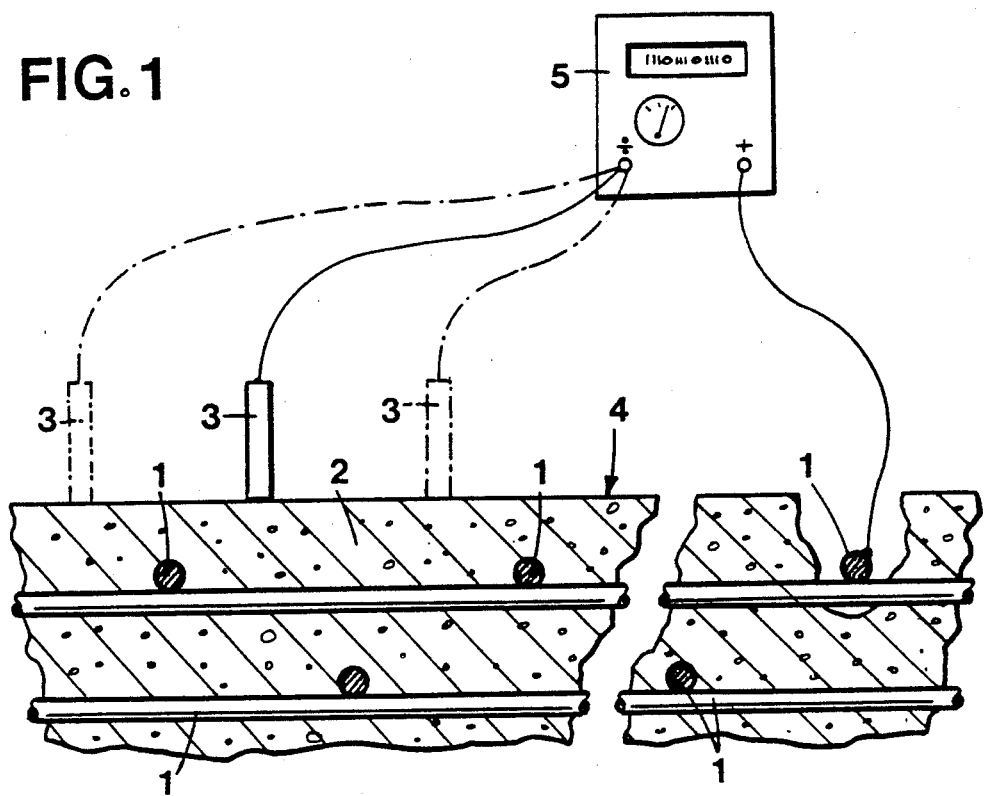
FIG. 1 is a schematic illustration of a first embodiment of the invention.

According to the invention, the first step is to make a series of point measurements of the electrical potential of the metal of the strengthening elements 1 embedded in the concrete 2 by moving a reference electrode 3, for example an electrode of the Cu/CuSO$_4$ type, at regular intervals along the surface 4 of the structure in question. The surface which is most easily accessible, according to the working conditions, will be chosen for this purpose, e.g. the side of a wall or trench, the periphery of a concrete pile or the top or bottom face of the floor of a bridge.

The measurements will be made in contact with the surface in question, for example every meter, every 50 cm or less, according to the situation encountered; as a general rule, these measurements will be made at regular intervals along two orthogonal axes (for example x and y). These measurements are made with a customary voltmeter 5, preferably a voltmeter of high internal resistance, one of the terminals of the said voltmeter 5 being connected to one of the metal elements 1 of the structure, which has been exposed or is directly accessible, and the other terminal of the voltmeter being connected to the reference electrode 3. The electrode 3 can be moved by any appropriate means or quite simply by hand; it will be described in detail later. The preferred reference electrode is an electrode of the Cu/CuSO$_4$ type, but it is also possible to use a calomel electrode or an electrode of the Ag/AgCl type.

According to the invention, the measurements made are then plotted on any suitable medium, for example graph paper, in order to set up a two-dimensional matrix such as that illustrated in FIG. 3. This kind of matrix contains series of values which are more or less homogeneous in places, as well as zones in which the measured values vary greatly from point to point.

When using a reference electrode 3 of the Cu/CuSO$_4$ type, steel bars 1 embedded in concrete 2 were found to be free of corrosion if the measured electrical potential was greater than about −200 mV, corrosion of the metal appearing at a potential of between −200 and about −300 mV. Actual corrosion is present at a potential below −300 mV. It is thus possible, by means of the two-dimensional matrix mentioned above, to delimit one or more surface zones 6, 6a, 6b, 6c . . . where the measured electronegative potential is below a limiting value, which in this case is −200 mV.

Figure 4:
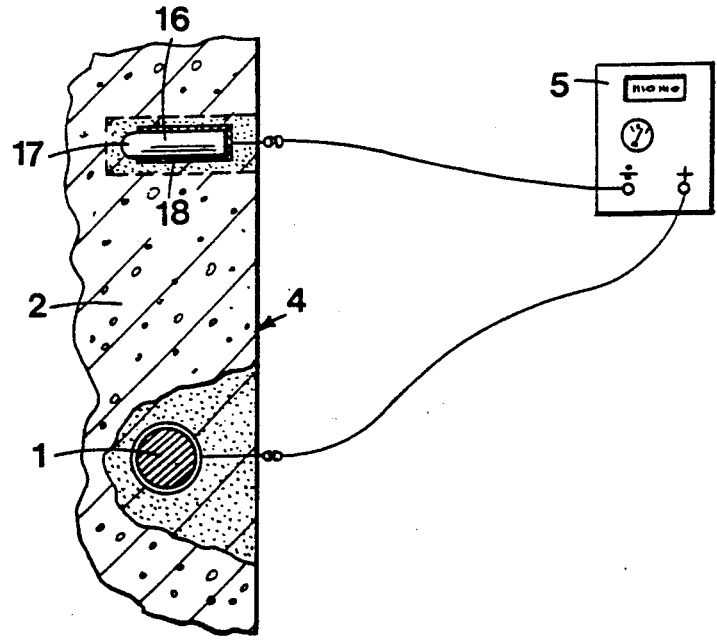
FIG. 4 is a schematic illustration of another embodiment of the invention.

According to the invention, once the surface zone 6, 6a, 6b . . . has been delimited, one or more point measurements of the relative moisture content of the concrete mass are made below the surface and within the zone defined above, the humidity of the ambient air being taken as the reference value. These measurements can be made by any customary means, for example using an electronic probe 20 placed in a sealed hole (e.g., sealed as by a plug 22) made in the concrete mass. A relative moisture content of more than 45% in the concrete was found to create a medium favoring the development of steel corrosion. These measurements can of course be made at any depth, according to the situation encountered. One suitable instrument for measuring moisture content is readily available from Vaisala Oy of Helsinki, Finland, and is sold under the trademark "HUMICAP" humidity instrument. Such an instrument includes a probe such as the probe 20 and a meter unit illustrated at reference numeral 21 in FIG. 4.

Thus, according to the invention, the zones of concrete which require treatment are determined as follows:

zones liable to be damaged by corrosion of the metal strengthening elements: measured electronegative potential between about −200 and about −300 mV and relative moisture content greater than about 45% (6, 6a, 6b . . . );

zones damaged by corrosion of the metal strengthening elements: measured electronegative potential below about −300 mV and relative moisture content greater than about 45% (7, 7a, 7b . . . ).

The zones located in this way can be treated by the customary techniques adapted to the circumstances encountered, especially according to the degree of metal corrosion and concrete damage found. Depending on the particular case, the said treatment will be purely preventive or a zone will be more or less extensively repaired. Types of treatment which may be mentioned are cathodic protection, coating or sealing of a portion of concrete, or even replacement of a portion of damaged concrete by fresh mortar, optionally in combination with an anticorrosion treatment of the metal elements involved.

A treatment which is both preventive (zones liable to be damaged) and restoring (zones actually damaged), and which is suitable for numerous situations, consists in coating the portion of surface delimited according to the process of the invention, or a larger portion, with a polymerized synthetic material which is preferably impervious to water and air, for example an epoxy resin or a polyurethane resin.

The reference electrode 3 used to carry out the above process is of the $Cu/CuSO_4$ type. It comprises a central electrode 8 made of copper metal, immersed in a saturated aqueous solution of $CuSO_4$, 9, at its upper end 10 an inflatable chamber 11 immersed in the solution 9, and at its lower end 12 a porous plug 13 in contact with the $CuSO_4$ solution 9.

The electrode 3 also comprises a leaktight plug 14 at its upper end and, of course, a cable 15 connecting it to the voltmeter 5. By virtue of this novel arrangement, the porous plug 13 remains permanently impregnated with $CuSO_4$ solution and the electrode 3 can be placed in any position without upsetting the precision of the measurement. Any zone of the surface to be inspected can thus be reached easily.

In another embodiment of the invention, the effectiveness of the above treatments can be continuously or intermittently monitored by the following procedure: one or more reference electrodes 16 are implanted in the concrete mass 2 and each of the said electrodes 16 is connected to an instrument for measuring the electrical potential, 5, which is itself connected to a metal strengthening element 1 embedded in the concrete 2. As previously, a voltmeter 5 of high internal resistance is preferably used for the measurements of electrical potential. As the reference electrode 16, it is possible to use any suitable referene electrode, in particular an electrode of the $Cu/CuSO_4$ type defined above. Another advantageous possibility is to use a lead electrode, which is implanted in the concrete mass at the desired spot. In FIG. 3, the spots marked with an asterisk (*) identify the location of a lead electrode 16. This is generally sealed in the concrete mass with fresh mortar, only its end 17 being in contact with the concrete and the remaining part being protected by an insulating material 18, for example a plastic coating.

As regards steel corrosion, the measured electrical potentials were found to correspond as follows:

| $Cu/CuSO_4$ | Pb |
|---|---|
| > −200 mV > +515 mV: | no corrosion |
| −200 to −300 mV +515 to +415 mV: | incipient corrosion |
| < −300 mV < +415 mV: | substantial corrosion |

The effectiveness of the treatment applied to the damaged concrete or concrete which is liable to be damaged will therefore be related to the measurement of the corrosion potential: such a process can be used, for example, to follow the regression of corrosion of the metal elements with time. Also, the need to treat concrete can be detected in time by means of measurement made at regular intervals, once certain limiting values have been exceeded.

An actual example is given below to illustrate one of the numerous applications of the invention.

EXAMPLE

Figure 2:
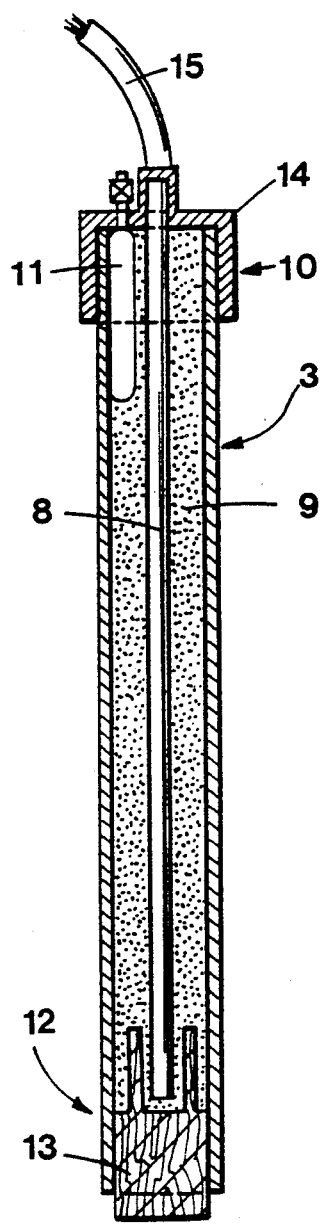
FIG. 2 is a cutaway view of the device used to carry out the process of the invention.

Electrical potential measurements were made on the bottom face of the floor of a reinforced concrete bridge using a $Cu/CuSO_4$ reference electrode such as that illustrated in FIG. 2. The potential was measured every 50 cm along two orthogonal axes and the measurements were then plotted on a paper medium. The matrix shown in FIG. 3 was thus obtained, giving the distribution of the electronegative potential values recorded (mV).

The shaded zones 6a, 6b, 6c . . . are those in which the potential measured on the surface is less than −200 mV, the boxed zone 7a being that in which the measured potential is less than −300 mV. The measurements of relative moisture content made by probing inside the zone 6a indicate a relative moisture content of 90%. Moreover, the surface of the boxed zone 7a was found to exhibit significant deterioration in the form of cracks due to corrosion of the metal of the strengthening bars.

To treat the concrete, four lead electrodes were then implanted in the concrete, inside the zone 6a, one of the electrodes being inside the boxed zone 7a. The location of these electrodes is given by an asterisk (*): the measured electrical potential is between +380 mV and +423 mV prior to treatment.

The zone 6a (potential less than −200 mV) was coated with a polyurethane resin and, after a few days, the recorded electrical potentials reached about +560 mV. After an area of concrete exceeding the zone 6a had also been coated, the potential measured after a few days reached +650 mV, signifying the effectiveness of the treatment applied.

Experience shows that such potential measurements are reliable, under the usual conditions, down to a depth of at least about 20 cm.

What I claim is:

1. A process for continuously or intermittently monitoring the effectiveness of the repairs made to zones of reinforced concrete structures, which comprises implanting one or more lead reference electrodes (16) in the concrete (2) and connecting each of the said electrodes (16) to an instrument (5) for measuring electrical potential, the said instrument itself being connected to a metal strengthening element (1) embedded in the concrete (2).

* * * * *